United States Patent [19]

Giddings et al.

[11] 4,347,182

[45] Aug. 31, 1982

[54] PREPARATION OF PENICILLANIC ACID DERIVATIVES

[75] Inventors: Peter J. Giddings, Westbury; David I. John, Epsom Downs; Eric J. Thomas, Oxford, all of England

[73] Assignee: Beecham Group Limited, England

[21] Appl. No.: 133,627

[22] Filed: Mar. 24, 1980

[30] Foreign Application Priority Data

Mar. 29, 1979 [GB] United Kingdom ............... 7911038
May 3, 1979 [GB] United Kingdom ............... 7915469
Jan. 7, 1980 [EP] European Pat. Off. ......... 80300067.8
Jan. 10, 1980 [JP] Japan ................................. 55/1720

[51] Int. Cl.$^3$ ............................................. C07D 499/00
[52] U.S. Cl. ............................. 260/245.2 R; 424/270
[58] Field of Search ................... 260/245.2 R; 424/270

[56] References Cited

U.S. PATENT DOCUMENTS 4,180,506 12/1979 Oratt ............................... 260/245.2
4,203,992 5/1980 Gordon et al. ................... 260/245.2

OTHER PUBLICATIONS

JCS Oerkin 1, 1976, p. 704.

*Primary Examiner*—Nicholas S. Rizzo
*Attorney, Agent, or Firm*—Jacobs & Jacobs

[57] ABSTRACT

The compound 6-β-chloropenicillanic acid can be prepared in substantially pure form and is a β-lactamase inhibitor which may be used to enhance the effectiveness of penicillins acid cephalosporins against β-lactamase producing lacteria.

The process comprises the reaction of a compound of the formula:

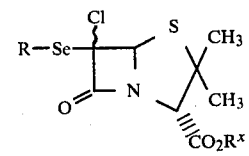

wherein $R^x$ is hydrogen or a carboxyl-blocking group and R is an aryl group, with a trialkyl tin hydride or a triaryl tin hydride or a dialkyl tin dihydride and optionally removing any carboxyl-blocking group $R^x$, and/or oxidizing the atoms to an SO or $SO_2$; and/or esterifying a salt of the acid to yield an in-vivo hydrolysable ester.

5 Claims, No Drawings

PREPARATION OF PENICILLANIC ACID DERIVATIVES

This invention relates to penicillanic acid derivatives and in particular to a class of 6β-chloropenicillanic acid derivatives.

Cartwright et al. (Nature, Vol. 278, 22 March 1979, page 360) reported that 6-α-chloropenicillanic acid was not an inhibitor of β-lactamase. The preparation of benzyl 6β-chloropenicillanate as a by-product in low yield has been described by Roets et al. (*J.C.S. Perkin I*, 1976, page 704) No utility has been suggested for this compound.

It has now been found that 6-β-chloropenicillanic acid can be prepared in substantially pure form and is a β-lactamase inhibitor which may be used to enhance the effectiveness of penicillins and cephalosporins against β-lactamase producing bacteria.

The present invention provides the compounds of the formula (I):

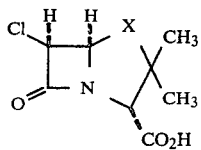

wherein X is S, SO or $SO_2$ and pharmaceutically acceptable salts and in-vivo hydrolysable esters thereof when substantially free from the corresponding 6-α-chlorocompound.

When used herein the term "substantially free" means that the 6-β-chloro-compound does not contain more than 15% w/w, more suitably not more than 10% w/w and preferably not more than 5% w/w of the 6-α-chlorocompound. The quantity of 6-α and 6-β isomers present may be determined by standard analytical techniques such as n.m.r. spectroscopy or h.p.l.c.

Favourably X in the compounds of the formula (I) is S or $SO_2$, preferably a sulphur atom.

The compounds of the formula (I) may be in the form of the free acid.

Alternatively the compounds of the formula (I) may be in the form of a pharmaceutically acceptable salt such as a metal salt, e.g. aluminium, alkali metal salts such as sodium or potassium, alkaline earth metal salts such as calcium or magnesium, and ammonium or substituted ammonium salts for example those with lower alkylamines such as triethylamine, hydroxy-lower alkylamines such as 2-hydroxyethylamine, bis-(2-hydroxyethyl)-amine, tris (hydroxymethyl)amine or tris-(2-hydroxyethyl)-amine, cycloalkylamines such as bicyclohexylamine, or with procaine, dibenzylamine, N,N-dibenzylethylenediamine, 1-ephenamine, N-ethylpiperdine, N-benzyl-β-phenethylamine, dehydroabietylamine, N,N'-bis-dehydroabietylethylenediamine, or bases of the pyridine type such as pyridine, collidine or quinoline, or other amines which have been used to form salts with penicillins.

Preferably the compounds of the formula (I) are in the form of a pharmaceutically acceptable salt such as the sodium, potassium, calcium or magnesium salt.

Suitable in-vivo hydrolysable esters include those esters known to give in-vivo hydrolysis in penicillins. Such esters are those which hydrolyse in the human body to produce the parent acid. Thus suitable esters include those of the sub-formulae (a), (b) and (c):

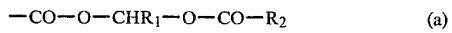

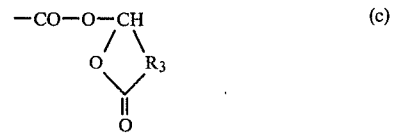

wherein $R_1$ is a hydrogen atom or a methyl group, $R_2$ is an alkyl group of up to 4 carbon atoms or a phenyl or benzyl group and $R_3$ is a 1,2-phenylene or a 4,5-dimethoxy-1,2-phenylene group.

Favourably $R_1$ is hydrogen.

When $R_1$ is hydrogen suitably $R_2$ is selected from methyl, ethyl, n-propyl, iso-propyl, n-butyl, tertbutyl, phenyl, benzyl, methoxy, ethoxy, n-propyloxy and iso-propyloxy. Preferably $R_2$ is tert-butyl.

Favourably $R_1$ and $R_2$ are joined so that the ester is a phthalidyl or 3,4-dimethoxyphthalidyl ester.

Thus preferred in-vivo hydrolysable ester groups include acetoxymethyl, pivaloyloxymethyl, α-acetoxyethyl, α-acetoxybenzyl, α-pivaloyloxyethyl, ethoxycarbonyloxymethyl, α-ethoxycarbonylethyl, phthalidyl and 5,6-dimethoxyphthalidyl.

Other suitable in-vivo hydrolysable groups include dialkylamino alkyl groups such as dimethylaminomethyl dimethylaminoethyl, diethylaminomethyl and diethylaminoethyl; and N-phthalimidomethyl and methoxymethyl groups.

The in-vivo hydrolysable nature of the ester may be confirmed by administration to an animal such as a mouse or rat and determination of the presence of 6-β-chloropenicillanate in the blood or urine of the animal. Alternatively hydrolysis in human blood or serum may be determined.

The methoxymethyl ester is also of use as an intermediate for the preparation of salts of the compounds of the formula (I) as described hereinbelow.

The present invention also provides a pharmaceutical composition which comprises a compound of the formula (I) or a pharmaceutically acceptable salt or in-vivo hydrolysable ester as hereinbefore defined and a pharmaceutically acceptable carrier.

The composition of this invention may be adopted for administration by injection or by the oral route.

Generally the composition will be presented as a unit dose containing from 60 to 600 mgs. of the β-lactamase inhibitor, more suitably 100 to 500 mgs. of the β-lactamase inhibitor and preferably from 125 to 300 mgs. of the inhibitor. Such compositions may be administered 2–6 times daily and usually 3 or 4 times daily in a manner such that the total daily dose for a 70 kg human will be about 200 to 1000 mgs.

The composition of this invention may be administered concurrently or consecutively with a penicillin or cephalosporin. However, it is greatly preferred to administer the penicillin or cephalosporin in the same composition as the β-lactamase inhibitor of this invention. British Patent Specification No. 1,508,978 discloses suitable penicillins and cephalosporins for use in such synergistic compositions. The forms of compositions, methods of preparation and ratios of components disclosed in Specification No. 1,508,978 may be also used with the synergists of this invention. The disclosures of Specification No. 1,508,978 with respect to compositions are accordingly incorporated herein by reference. A suitable penicillin is amoxycillin as the trihydrate or sodium salt.

The present invention also provides a process for the preparation of a compound of the formula (I) or a pharmaceutically acceptable salt or in-vivo hydrolysable ester thereof, which process comprises the reaction of a compound of the formula (II):

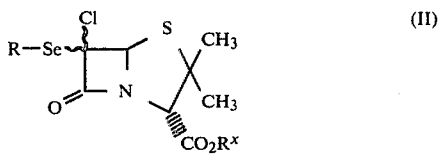
(II)

wherein $R^x$ is hydrogen or a carboxyl-blocking group and R is an aryl group, with a trialkyl tin hydride or a triaryl tin hydride or a dialkyl tin dihydride, and thereafter optionally removing any carboxyl-blocking group $R^x$, and/or oxidizing the S atom to an SO or $SO_2$ group; and/or esterifying a salt of the compound of the formula (I) to yield an in-vivo hydrolysable ester thereof.

A great advantage of this process is that it provides the desired 6β-isomer substantially free of the 6α-isomer.

Suitably the hydride is a tri-$C_{1-6}$ alkyl tin hydride. When used herein the term "aryl" means a phenyl group or a phenyl group substituted by $C_{1-3}$ alkyl, $C_{1-3}$ alkoxy, hydroxy or nitro. A preferred triaryl tin hydride is triphenyl tin hydride. Another preferred reagent is tri-n-butyl tin hydride.

A preferred group R is phenyl.

The reaction is generally carried out in an inert organic solvent such as benzene or toluene at an elevated temperature such as 80° to 110° C. Generally the reaction mixture also comprises azobisisobutyronitrile (A B I B N). The initial crude product may be obtained by evaporation of the solvents. Chromatography may be used to obtain the purified product.

Suitable carboxyl blocking groups $R^x$ are ester groups which are compatible with the use of tin hydrides and include benzyl, p-methoxybenzyl, 2,4,6-trimethylbenzyl, benzoylmethyl, 4-pyridylmethyl, 2,2,2-trichloroethyl, t-butyl, t-amyl, diphenylmethyl, triphenylmethyl, adamantyl, 2-benzyloxyphenyl, 4-methylthiophenyl, methoxymethyl, tetrahydrofur-2-yl, tetrahydropyran-2-yl, pentachlorophenyl, silyl groups such as trimethylsilyl or 5-butyldiphenylsilyl, trialkyl tin esters or oxime ester radicals of formula N=CHR° where R° is aryl or heterocyclic.

The carboxyl group may be regenerated from any of the above esters by usual methods appropriate to the particular ester group, for example, acid—and base—catalysed hydrolysis, or by enzymically—catalysed hydrolysis, or by hydrogenation.

A preferred ester of the compound of the formula (II) is the 2,2,2-trichloroethyl ester. The resulting acid may be carefully neutralised to provide salts. These salts may be re-esterified in conventional manner such as the reaction of a reactive halide with the salt in dimethylformamide to provide in-vivo hydrolysable esters of formula (I).

The sulphur atom may be oxidized in conventional manner, for example with m-chloroperbenzoic acid.

An ester of formula (II) may be prepared as outlined in the following Scheme:

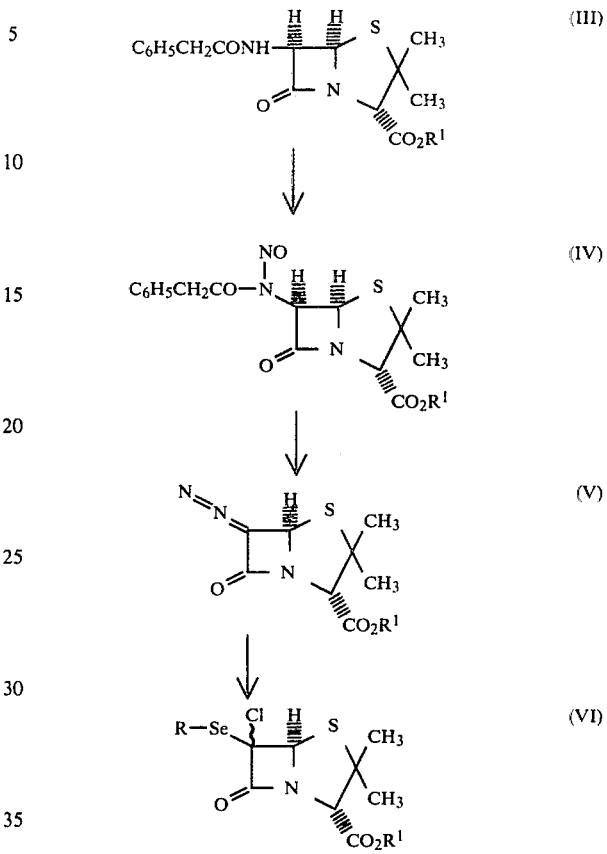

in the preceding Scheme $R^1$ is a group such that $CO_2R^1$ is a cleavable ester group.

The conversion (III)–(IV) may be effected by treatment of (III) with dinitrogen tetroxide in an inert solvent such as dichloromethane at a depressed temperature such as 0° to −10° C. The compound (IV) is reactive and is best used immediately after preparation, for example it may be warmed in an inert solvent such as dichloromethane until it is converted into the compound (V).

A compound of the formula (V) may be converted into a compound of the formula (VI) by reaction with an aryl selenyl chloride in an inert solvent such as dichloromethane at an ambient temperature. Evaporation of the solvent produces an initial crude product which may be purified by crystallisation, chromatography or the like.

The preceding reaction sequence may be carried out without isolation and purification of intermediates; preferably the compound of formula (V) is isolated and purified.

The following Examples illustrate this invention.

EXAMPLE 1

2,2,2-Trichloroethyl 6β-chloropenicillanate (i) 2,2,2-Trichloroethyl 6β-phenylacetamidopenicillanate The potassium salt of benzylpenicillin (44.52 g, 0.119 M) was suspended in 600 ml of dry methylene chloride. A slurry of pyridinium chloride (14.40 g, 0.119 M) in 60 ml CH$_2$Cl$_2$ was added. A solution of trichloroethanol (18.0 g, 0.119 M) in 60 ml of CH$_2$Cl$_2$ and then dicyclohexylcarbodi-imide (24.72 g, 0.119 M) in 120 ml CH$_2$Cl$_2$ were added. The mixture was stirred for 17 hrs at room temperature and then filtered. The filtrate was washed with 5% sodium bicarbonate (3×200 ml), water (1×200 ml), dried (MgSO$_4$) and the solvent removed under reduced pressure. The resultant crude yellow/brown solid was recrystallised from ethyl acetate/petroleum ether (60–80) to give the ester as white crystals 38.90 g (70%): m.p. 157°–158°; I.R. (CHCl$_3$): 3300, 1770 and 1690 cm$^{-1}$; NMR (CDCl$_3$) δ 1.49 (S, 6H) 3.55 (S, 3H) 4.45 (S, 1H) 4.76 (S, 2H) 5.50 (m, 2H) 6.30 (broad d, 1H) 7.20 (S, 5H).

(ii) 2,2,2-Trichloroethyl 6β-N-Nitrosophenylacetamidopenicillanate

Dinitrogen tetroxide (20 g, 0.217 M) was dissolved in 250 ml methylene chloride. Half of this was then added to a mixture of 2,2,2-trichloroethyl 6β-phenylacetamidopenicillanate (31.50 g, 0.067 mM) and sodium acetate (66 g, 0.80 M) in 350 ml CH$_2$Cl$_2$ and the mixture stirred for 1½ hrs at −5°. The remaining dinitrogen tetroxide was added after 45 mins. Excess dinitrogen tetroxide was destroyed by pouring onto sodium bicarbonate solution (60 g in 500 ml H$_2$O) slowly, with stirring over a period of approx 30 mins. The organic phase was washed with aq. sodium bicarbonate (1×500 ml) water (1×500 ml), dried (MgSO$_4$) and concentrated to approx. 350 ml. This is the N-nitrosophenylacetamidopenicillanate, which was not isolated but converted immediately to the diazo derivative.

(iii) 2,2,2-Trichloroethyl 6-diazopenicillanate 2,2,2-Trichloroethyl 6β-N-nitrosophenylacetamidopenicillanate was refluxed in methylene chloride for 4 hrs, allowed to cool, washed with aqueous sodium bicarbonate solution (3×250 ml), water (1×500 ml), dried (MgSO$_4$) and the solvent removed under reduced pressure to give the crude yellow solid diazo compound. Recrystallisation from ethanol gave the 2,2,2-trichloroethyl 6-diazopenicillanate as yellow crystals 12.42 g (51%): m.p. 103°–104°; IR (CHCl$_3$) 2100 and 1740 cm$^{-1}$; NMR δ 1.50 (S, 3H) 1.70 (S, 3H) 4.45 (S, 1H) 4.70 (S, 2H) 6.15 (S, 1H).

(iv) 2,2,2-Trichloroethyl 6-chloro-6-phenylselenylpenicillanate 2,2,2-Trichloroethyl 6-diazopenicillanate (1.5 g, 4.19 mM) was dissolved in 50 ml CH$_2$Cl$_2$ under a nitrogen atmosphere. Phenylselenyl chloride (0.802 g, 4.19 mM) in 25 ml CH$_2$Cl$_2$ was added, slowly, with stirring over 5–10 mins. There was an immediate evolution of nitrogen and simultaneous decolouration of the phenyl selenyl chloride. The mixture was then stirred for 15 min at room temperature, and the solvent removed under reduced pressure to give 1.7 g crude yellow/brown oil which slowly solidified. Recrystallisation from ethylacetate/petroleum ether (60–80) gave 2,2,2-trichloroethyl 6-chloro-6-phenylselenylpenicillanate as white crystals 1.6 g (53%): m.p. 115°–115.5°; IR (CHCl$_3$) 1780 and 1760 cm$^{-1}$, NMR (CDCl$_3$) δ 1.58 (S, 3H) 1.83 (S, 3H) 4.69 (S, 1H) 4.79 (S, 2H) 5.68 (S, 1H) 7.37 (m, 4H) 7.79 (m, 2H). Anal. Calculated for C$_{16}$H$_{15}$NO$_3$Cl$_4$ S se (522.20): C, 36.80; H, 2.89; N, 2.68; Cl, 27.16; S, 6.14. Found: C, 36.98; H, 3.03; N, 2.59; Cl, 26.88; S, 6.00: [α]$_D^{20}$= +89.83°.

(v) 2,2,2-Trichloroethyl 6β-chloropenicillanate 2,2,2-Trichloroethyl 6-chloro-6-phenylselenylpenicillanate (500 mg, 0.95 mM) was dissolved in dry benzene (about 25 ml). ABIBN (30 mg, 20 mol %) was then added, followed by tri-n-butyl tin hydride (290 mg, 1.10 mol). The solution was then heated to a gentle reflux for 1 hr under a nitrogen atmosphere (oil bath at 88°). TLC of the crude mixture showed two spots, and separation of the two by column chromatography on silica gel (15 g) in 5% ethyl acetate/petroleum ether (60–80) gave starting material (104 mg) and the required 6β-chloropenicillanate as a pale yellow oil (166 mg, 44%): IR (CHCl$_3$); 1785 and 1760 cm$^{-1}$; NMR (CHCl$_3$) δ 1.60 (S, 3H) 1.70 (S, 3H) 4.46 (S, 1H) 4.80 (S, 2H) 5.25 (d, 1H, J=4 Hz) 5.65 (d, 1H, J=4 Hz); [α]$_D^{20}$= +125°.

Complete reaction could not be achieved by increasing either the reaction time or the amount of ABIBN or nBu$_3$SnH.

EXAMPLE 2

6β-Chloropenicillanic acid 2,2,2-Trichloroethyl 6β-chloropenicillanate (100 mg, 0.27 mM) was dissolved in 90% acetic acid (5 ml). The solution was then cooled to 0° before zinc dust (acid washed, 1.0 g) was added. The mixture was then stirred at 0° for 4 hrs. The zinc was removed by filtration under vacuum into a flask containing 100 ml of ice water and washing of the zinc with 50 ml methylene chloride yielded a two phase system. The organic layer was separated off and the aqueous layer washed three times with methylene chloride (3×50 ml). The combined organic phases were dried (MgSO$_4$) and evaporated under reduced pressure (no heat) to give the free acid as a pale yellow oil.

For purification, the acid was dissolved in methylene chloride (50 ml) and extracted with aqueous sodium bicarbonate. The aqueous layer, after being extracted several times with methylene chloride (3×75 ml) was cooled in ice and acidified with dilute HCl (pH 1→2). Extraction with methylene chloride, drying (MgSO$_4$) and removal of solvent under reduced pressure (no heat) afforded the pure acid, as an offwhite solid 38 mg (60%). [α]$_D$+256° (0.2% in CHCl$_3$), ν$_{max}$(CHCl$_3$) 2 600 (OH), 1 790 (β-lactam C=O), 1 730 (acid C=O), 1 300 cm$^{-1}$; δ (CDCl$_3$) 1.58 and 1.69, (each 3 H, S, gem-Me$_2$), 4.54 (1 H, S, NCHCO$_2$H), 5.23 (1 H, d, J 3.8 Hz, ClCHCHS), 5.60 (1 H, d, J 4.1 Hz, ClCHCHS), 7.26 br (1 H, S, CO$_2$H) [addition of D$_2$O causes the signal at 7.26 to disappear]; $^m$/e 237, 235 (M$^+$), 160 (M$^+$-ClC±=C=O) and 100 (100%).

EXAMPLE 3

2,2,2-Trichloroethyl 6β-chloropenicillanate 1,1-dioxide 2,2,2-Trichloroethyl 6β-chloropenicillanate (168 mg, 0.48 mM) was dissolved in anhydrous dichloromethane (10 ml). m-Chloroperoxybenzoic acid (1.97 mg, 1.14 mM) was added, and the reaction mixture stirred at room temperature for 24 h. The reaction mixture was then diluted with dichloromethane (20 ml), washed with aqueous sodium bicarbonate, then water, dried (MgSO$_4$), and evaporated in vacuo to give a white solid (119 mg, 80%). Recrystallisation from ethyl acetate—light petroleum, gave white crystals of 2,2,2-trichloroethyl 6β-chloropenicillanate 1,1-dioxide (95 mg, 64%), m.p. 157°–158° C., [α]$_D$+157° (0.7% in CHCl$_3$), ν$_{max}$ (CHCl$_3$) 1820 (β-lactam C=O), 1 770 (ester C=O), 1 340

(SO$_2$), 1 180, 810 cm$^{-1}$, δ (CDCl$_3$) 1.50 and 1.70 (each 3 H, S, gem-Me$_2$), 4.71 (1 H, d, J=4 Hz, ClCHCHS), 4.85 (2 H, q, J 4.7 and 19.6 Hz, CO$_2$CH$_2$C Cl$_3$), 4.96 (1 H, S, NCHCO$_2$CH$_2$ Cl$_3$), 5.39 (1 H, d, J 4.1 Hz, ClCHCHS); $m/e$ 401, 399, 397 (M$^+$-Cl), and 100 (100%) (Found: C, 30.11; H, 2.93; Cl, 35.29; N, 3.32; S, 8.18. C$_{10}$H$_{11}$$^{35}$Cl$_4$NO$_5$S requires C, 30.09; H, 2.78; Cl, 35.54; N, 3.51; S, 8.03%).

EXAMPLE 4

Preparation of Benzyl 6β-chloropenicillanate 1,1-dioxide

Benzyl 6β-chloropenicillanate (300 mg, 0.92 mM) was dissolved in anhydrous dichloromethane (15 ml). m-Chloroperoxybenzoic acid (397 mg, 2.3 mM) was added, and the reaction mixture stirred for 24 h at room temperature. Work-up as in example 36, followed by column chromatography on silica-gel (ethyl acetate—light petroleum (1:9) as eluant) gave, as a colourless oil, benzyl (6β-chloropenicillanate, 1,1-dioxide (316 mg, 96%) [α]$_D$+193° (1% in CHCl$_3$), $ν_{max}$ (CHCl$_3$) 1 810 (β-lactam C=O), 1 745 (ester C=O), 1 460, 1 340 (SO$_2$), 1 120 (SO$_2$), 700 cm$^{-1}$; δ (CDCl$_3$) 1.25 and 1.54 (each 3 H, S, gem-Me$_2$), 4.56 (1 H, S, NCHCO$_2$CH$_2$Ph), 4.77 (1 H, d, J 4.7 Hz, ClCHCHS), 5.23 (2 H, q, J 4.4 and 9.0 Hz, CO$_2$CH$_2$Ph), 5.33 (1 H, d, J 4.7 Hz, ClCHCHS), 7.38 (5 H, S, CO$_2$CH$_2$Ph); $m/e$ 358, 356 (M$^+$) and 91 (100%, C$_7$H$_7$$^+$).

EXAMPLE 5

Benzyl 6β-chloropenicillanate

Benzyl 6-chloro-6-phenylselenylpenicillanate (900 mg, 1.9 mM) was dissolved in anhydrous benzene (20 ml). ABIBN (62 mg, 0.37 MM) was added, followed by tri-n-butyltin hydride (607 mg, 2.08 mM). The solution was then heated under reflux under a nitrogen atmosphere for 1.5 h. Evaporation of solvent in vacuo gave a colourless oil which showed a single component in addition to the tri-n-butyltinphenylselenium residues. Purification of the crude product by column chromatography on silica-gel [ethyl acetate—light petroleum (1:19) as eluant] gave, as a colourless oil, benzyl 6β-chloropenicillanate (448 mg, 74%), [α]$_D$+249° (1% in CHCl$_3$), $ν_{max}$ (CHCl$_3$) 1 790 (β-lactam C=O), 1 740 (ester C=O), 1 500, 1 460, 1 030, 760 (C-Cl) cm$^{-1}$; δ (CDCl$_3$) 1.35 and 1.55 (each 3 H, S, gem-Me$_2$), 4.50 (1 H, S, NCHCO$_2$CH$_2$Ph), 5.15 (2 H, S, CO$_2$CH$_2$Ph), 5.17 (1 H, d, J 4 Hz, ClCHCHS), 5.55 (1 H, d, J 4 Hz, ClCHCHS), 7.30 (5 H, S, CO$_2$CH$_2$Ph ); $m/e$ 326, 324, (M$^+$), 251, 249 (M$^+$-ClC$^+$=C=O), and 91 (100%, C$_7$H$_7$$^+$) (Found: M$^+$, 325.0513. C$_{15}$H$_{15}$$^{35}$ClNO$_3$S requires M, 325.0530).

EXAMPLE 6

6β-Chloropenicillanic acid 1,1-dioxide

Benzyl 6β-chloropenicillanate 1,1-dioxide (100 mg, 0.28 mM) was dissolved in ethyl acetate and 10% Pd/C catalyst (100 mg) added to it. The mixture was then placed in an atmosphere of hydrogen at 55 p.s.i. for 1.5 h. The catalyst was removed by filtration, and the solvent evaporated in vacuo to yield, as a white foam, 6β-chloropenicillanic acid 1,1-dioxide (60 mg, 80%), $ν_{max}$ (nujol) 2 600, 2 400 (OH), 1 810 (β-lactam C=O), 1 340 (SO$_2$), 1 120 (SO$_2$), 1 000, 840 cm$^{-1}$; δ[(CD$_3$)$_2$C=O)] 1.48 and 1.60 (each 3 H, S, gem-Me$_2$), 4.54 (1 H, S, CHCO$_2$H), 5.26 (1 H, d, J 4.4 Hz, ClCHCHS), 5.83 (1 H, d, J 4.11 Hz, ClCHCHS), 6.8 br (1 H, S, OH) [addition of D$_2$O causes the signal at 6.8 to disappear]; $m/e$ 269,267 (M$^+$) and 100 (100%).

Description 1

Biological Properties of 6β-Chloropenicillanic Acid

The MIC of ampicillin against certain ampicillin resistant bacteria was determined in the presence of 6β-chloropenicillanic acid. The results obtained were as follows:

| | MIC (μg/ml) of Ampicillin | | | |
|---|---|---|---|---|
| Inhibitor Conc. (μg/ml) | Staph. aureus Russell | Klebsiella aerogenes E70 | Proteus sp. C889 | E. coli J T 39 |
| 20 | (0.1) | 12.5 | 31 | 500 |
| 5 | 0.78 | 25 | 500 | 500 |

This product was tested as an inhibitor of various β-lactamases using a chromogenic cephalosporin as substrate. Pre-incubation of cell-free preparations of the enzymes with the inhibitor resulted in inhibition of the hydrolytic action of all four enzyme preparations studied. For the Staphylococcus Russell and *Klebsiella aerogenes* E 70 enzymes the concentrations of inhibitor required to produce 50% inhibition of hydrolysis were 0.3 μg/ml and 6.5 μg/ml and 6.5 μg/ml respectively. With the Enterobacter P 99 and *Escherichia coli* JT 4 enzyme preparations, 50 μg/ml of inhibitor produced 31% and approximately 42% inhibition respectively.

What we claim is:
1. A process for the preparation of a compound of the formula (I):

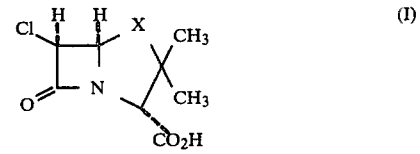

wherein X is S, SO or SO$_2$, or a pharmaceutically acceptable salt or in-vivo hydrolysable ester thereof which process comprises reacting compound of the formula (II):

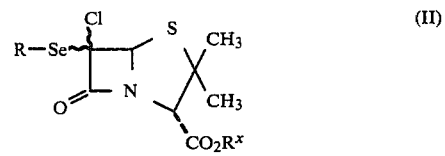

wherein R$^x$ is hydrogen or a carboxyl-blocking group and R is phenyl unsubstituted or substituted by C$_{1-3}$ alkyl, C$_{1-3}$ alkoxy, hydroxy or nitro to deselenate it without 6-dehalogenation with a trialkyl tin hydride or a dialkyl tin dihydride or triphenyl tin hydride wherein the phenyl groups are unsubstituted or substituted by C$_{1-3}$ alkyl, C$_{1-6}$ alkoxy, hydroxy or nitro, and thereafter optionally removing any carboxyl-blocking group R$^x$; and/or oxidising the S atom to an SO or SO$_2$ group; and/or esterifying the salt of the compound of the formula (I) to yield an in-vivo hydrolysable ester thereof.

2. A process according to claim 1 wherein R is a phenyl group.

3. A process according to claim 1 wherein the reducing agent is a trialkyl tin hydride.

4. A process according to claim 3 wherein the reducing agent is tri-n-butyl tin hydride.

5. A process according to claim 1 wherein the reducing agent is triphenyl tin hydride.

* * * * *